United States Patent [19]
Akashi et al.

[11] Patent Number: 5,686,385
[45] Date of Patent: Nov. 11, 1997

[54] AGRICULTURAL MICROCAPSULE AND PRODUCTION THEREOF

[75] Inventors: Kanji Akashi; Chikara Tanabayashi; Kazutaka Kitagawa, all of Tsukuba, Japan

[73] Assignee: Takeda Chemical Industries, Ltd., Osaka, Japan

[21] Appl. No.: 461,423

[22] Filed: Jun. 5, 1995

Related U.S. Application Data

[62] Division of Ser. No. 992,005, Dec. 17, 1992.

[30] Foreign Application Priority Data

Dec. 27, 1991 [JP] Japan .................................. 4-346658

[51] Int. Cl.$^6$ ......................................... A01N 25/28
[52] U.S. Cl. ....................... 504/116; 514/721; 514/772.2; 514/778; 514/782; 514/963; 424/485
[58] Field of Search ........................ 504/116; 71/DIG. 1; 514/94, 132, 357, 366, 473, 564, 567, 649, 721, 772.2, 778, 782, 963; 424/485

[56] References Cited

U.S. PATENT DOCUMENTS

| | | | |
|---|---|---|---|
| 3,780,170 | 12/1973 | Goodhart et al. | 424/35 |
| 4,230,687 | 10/1980 | Sair et al. | 424/22 |
| 4,244,836 | 1/1981 | Frensch et al. | 252/316 |
| 4,380,626 | 4/1983 | Szejtli et al. | 536/103 |
| 4,462,839 | 7/1984 | McGinley et al. | 106/198 |
| 4,696,822 | 9/1987 | Matsumura et al. | 424/490 |
| 4,790,990 | 12/1988 | Mason et al. | 424/438 |

FOREIGN PATENT DOCUMENTS

| | | |
|---|---|---|
| 0 141 509 | 5/1985 | European Pat. Off. . |
| 38-0325 | 8/1990 | European Pat. Off. . |
| 24-96403 | 6/1982 | France . |
| 38-16865 | 11/1989 | Germany . |
| 58-90502 | 5/1983 | Japan . |
| 20-13610 | 8/1979 | United Kingdom . |

OTHER PUBLICATIONS

Sliwka, "Microencapsulation." *Angewandte Chemie* International Edition. 14(8):539–550. 1975.
Bakan et al. "Part III. Microencapsulation," in Lachman et al, ed. *The Theory and Practice of Industrial Pharmacy*, 2nd ed. 1976.
Szetli "Industrial Applications of Cyclodextrins" Ch. 11 of *Inclusion Compounds*, Atwood et al. ed. Academic Pr. pp. 331–389. 1984.
Pitha et al "Molecular Encapsulation of Drugs by Cyclodectrins..." Ch. 5. of Bruck, ed. *Controlled Drug Delivery*. CRC Pr. pp. 125–148. 1983.
WPI Acc. No. 73–64756U/43, Patent Abstract of Japan, 48–052943, (1973).
WPI Acc. No. 78–44930A/25, Patent Abstract of Japan, 53–052626, (1978).
WPI Acc. No. 79–74590B/41, Patent Abstract of Japan, 54–113438, (1979).
WPI Acc. No. 83–702944/27, Patent Abstract of Japan, 58–090502, (1983).
WPI Acc. No. 83–811970/45, Patent Abstract of Japan, 58–167502, (1983).
WPI Acc. No. 89–050475/07, Patent Abstract of Japan, 64–000009, (1989).
WPI Acc. No. 90–080951/11, Patent Abstract of Japan, 20–36102, (1990).
WPI Acc. No. 77–13719Y/08, Patent Abstract of Japan, 52–003833, (1977).
Central Patents Index, Basic Abstracts Journal, Section Ch, Week 8408, 18 Apr. 1984, Derwent Publications Ltd., JP-A-59 007-101, Abstract.
Chemical Patents Index, Basic Abstracts Journal, Section Ch, Week 8613, 21 May 1986, Derwent Publications Ltd., JP-A-61 030 502, Abstract.
Chemical Patents Index, Documentation Abstracts Journal, Section Ch, Week 9011, 9 May 1990, Derwent Publications, Ltd., JP-A-02 036 102, Abstract.
Central Patents Index, Basic Abstracts Journal, Section Ch, Week 7802, Derwent Publications Ltd., JP-A-77 048 180, Abstract, Dec. 1977.
Lachman et al., The Theory and Practice of Industrial Pharmacy, 2nd ed. pp. 420–438, "Microencapsulation", (1976).
The Agrachemicals Handbook "Ferimzone", Aug. 1991.

*Primary Examiner*—S. Mark Clardy
*Attorney, Agent, or Firm*—Foley and Lardner

[57] ABSTRACT

The present invention provides microcapsule comprising agricultural active ingredients with improved physical properties, and an agricultural composition comprising said microcapsule. An agricultural microcapsule having a diameter of not more than 50 μm comprises an agricultural active ingredient in a water-soluble coating material. As an agricultural composition comprising said microcapsules, DL dust, solidified emulsifiable concentrate can be provided.

According to the present invention, the agricultural active ingredient is stabilized, agricultural dust can be mixed with even incompatible, liquid agricultural active ingredient, and agricultural microcapsule has excellent handling properties.

16 Claims, No Drawings

AGRICULTURAL MICROCAPSULE AND PRODUCTION THEREOF

This application is a divisional of application Ser. No. 07/992,005, filed Dec. 17, 1992.

The present invention relates to a novel agricultural microcapsule with improved physical and chemical properties which comprises an agricultural active ingredient, and production thereof.

[BACKGROUND OF THE INVENTION]

In general, pesticidal compositions include those containing a single pesticidal active ingredient and those containing two or more pesticidal ingredients. The former is expected to show a single effect. On the other hand, the latter compositions are expected to show superior effects to those shown by the individual ingredient, or labor-saving application. Particularly, the admixture containing two or more pesticidal active ingredients has been widely and generally used in the agricultural field. These single or mixed agricultural compositions usually are subjected to a long period after production before usage. During the period, the active ingredients in the composition may be decomposed, and accordingly the composition may lose its biological activity and sometimes may cause phytotoxicity.

For example, (Z)-2'-methylacetophenon=6-dimethylpyrimidin-2-ylhydrazone (hereinafter referred to as ferimzone) is known as an excellent agricultural fungicide which shows strong fungicidal activity for a wide range of plant pathogenic fungi such as *Pyricularia oryzae, Cochliobolus miyabeanus*, etc. (cf. Japanese Patent Publication No. 21551/1986). For control of rice stem bores, leaf hoppers, etc., it is well known that organophosphorus compounds such as 0,0-dimethyl-0-(3-methyl-4-nitrophenyl)phosphorothioate (hereinafter abbreviated to fenitrothion) and the like are effective. Accordingly, it is strongly expected to develop an admixture having biological activities of both of said two compounds. However, when the two compounds are mixed, the active ingredients are remarkably decomposed, after a long period of storage, and the admixture shows no biological activity. Especially, organophosphorus compounds are more decomposed with the passage of time. For control of such decomposition, agricultural compositions containing boron oxide and/or boron oxide complex are known (Japanese Patent Laying-Open No. 9/1989). However, boron oxide, a stabilizer, itself is very hygroscopic, and thus the physical stability of this preparation is not much improved.

An admixture of 5-methyl-1,2,4-triazolo[3,4-b]benzothiazole (hereinafter abbreviated to tricyclazole), which is a fungicide showing excellent effect on control of blast disease, etc., and an insecticidal organophosphorus compound such as fenitrothion is known. However, when the two compounds are admixed together, said two ingredients react with each other, resulting in chemical change and decomposition, and finally the composition shows no effective biological activity. Thus, for control of decomposition of the admixture containing tricyclazole and organophosphorus compound, an agricultural composition containing oxalic acid and/or benzenesulfonic acid is well known (Japanese Patent Laying-Open No. 167502/1983). Moreover, for saving labor, an admixture containing tricyclazole and fenitrothion as well as validamycin A in order to simultaneously control slimy brown rot of rice plant is expected to be developed. For such mixture, benzenesulfonic acid which is added to control decomposition of tricyclazole and fenitrothion disadvantageously decomposes validamycin A.

Recently, the development of agricultural admixture has acquired greater importance. However, some agricutural active ingredients are unstable under acidic conditions, while others are unstable under basic conditions. That is, the characteristics of active ingredients are generally different, and the methods to sufficiently stabilize active ingredients in admixture have not been developed.

For sufficient demonstration of the effect of the active ingredients in the agricultural preparations, particularly dust when applied as to plants, it is also important to improve dispersibility of such dust for effective and homogeneous application of the dust to plants.

However, for an admixture containing liquid agricultural active ingredients, physical properties such as flowability and dispersibility of the dust preparation may be deteriorated, accordingly, the preparation can not be sprayed homogeneously, resulting in bad effect and sometimes causing phytotoxicity.

Considering such conditions, methods to improve physical properties by adding fine powder of aerosil, white carbon etc. have been employed. However, in such methods, improvement of the physical properties of the preparation is difficult with more liquid content. Accordingly, study to improve physical properties of the preparation has been carried out. For example, dust composition containing one or more organophosphorus salts or ester (cf. Japanese Patent Laying-Open No. 113438/1979), dust composition for gardening containing polysiloxane (cf. Japanese Patent Laying-Open No. 90502/1983) and the like are known. However, effective methods for improvement of physical and chemical properties of the effective preparation of mixture containing more liquid active ingredients have not been attained.

The preparation in which an active ingredient was coated by wax was also provided in the prior art. But as wax is insoluble to water, it is very hard to control the release of the active ingredient from the preparation. Moreover, a preparation containing fine granules as powder cannot be provided by such a conventional method.

Accordingly, in the above-mentioned conventional methods, stabilization of pesticidal active ingredients has not been attained in a mixture of ferimzone and fenitrothion, a mixture containing tricyclazole and fenitrothion or other pesticide mixture preparations. Further, no improvement of the effective physical and chemical properties of a mixture containing liquid pesticidal active ingredients has been attained.

The processes for production of agricultural preparations by spray drying are described in, for example, Japanese Patent Laying-Open Nos. 52626/1978, 52948/1973 and 64904/1985). These references disclose processes for production to obtain granules of relatively large particle size by spray drying slurry wherein agricultural active ingredients coexist with solid carrier.

Preparations for solidifying a liquid agricultural ingredient such as an active ingredient have been prepared by impregnating or adsorbing the ingredient with a solid carrier. The above-mentioned preparation produced by spray-drying is also proposed with the object of impregnating or adsorbing an active ingredient with a solid carrier just by means of spray-drying. No conception to solidify an active ingredient itself is in the prior art. No solid preparation as powder is obtained by such a conventional method. Therefore, adversed problems have not solved sufficiently yet. Such problems are that imcompatible ingredients such as active ingredients, carriers, diluents, etc. interact each other and that the active ingredient is decomposed itself.

On the other hand, capsule preparations in the fields of medicines, perfumery or feed additive have been known (U.S. Pat. No. 4,230,687; Japanese Patent Laying-Open Nos. 24347/1986, 55816/1974, 69039/1985: Yoshiaki KAWASHIMA "Fine Particle Design-Technology", pub. by Powder and Industry Co., pp.86–96 (1988)). However, the above conventional methods have not discribed encapsulation of an agricultural active ingredient at all. In addition, there is no disclosure on whether or not the encapsulated pesticide can be effective in the field if an agricultural active ingredient were encapsulated according to the conventional method. Only Japanese Patent Laid-open No. 36102/1990 proposes a pesticidal admixture containing a microcapsulated active ingredient of average particule size of not more than 100 μm and powdery additive. In a specification of the patent application, however, there are only disclosures of conventional coating materials including water-soluble and water-insoluble ones, and no disclosure on what kind of microcapsules were obtained or used. How to make them also could not be found. It must be clarified that there is no investigation and no motivation on a microcapsule including water-soluble coating material in the prior application.

Accordingly, the prior art has not solved the problems of stabilization of the individual active ingredients and stabilization of incompatible compounding agents. Further, they provide no suggestion whether their technique can be applied for agricultural compositions.

[SUMMARY OF THE INVENTION]

The present invention solves such problems of the aforementioned conventional technique and provides an agricultural microcapsule wherein the active ingredients are stabilized. The microcapsule can be admixed with the other ingredient even if the other is incompatible to the active ingredient comprised in the microcapsule. The microcapsule provided in this invention is handled easily and has a good adhesiveness to a plant. Specially, when an active ingredient is a liquid such as oil, the active ingredient per se can be handled as a solid powder by means that the active ingredient is microencapsulated according to the present invention.

Further, the present invention provides an agricultural composition comprising the agricultural microcapsule. Especially, DL dust (Drift-Less) and solidified emulsifiable concentrate which are easily handled can be provided in the present invention.

Still further, the present invention provides an agricultural admixture composition comprising two or more agricultural active ingredients which are incompatible each other, by means that at least one active ingredient is microcapsulated according to the present invention.

Moreover, the present invention provides an useful process for production of the microcapsule which is spray-drying.

[DETAILED DISCRIPTION OF THE INVENTION]

The present inventors have studied intensively to obtain agricultural preparations comprising one or more agricutural active ingredients wherein decomposition of the active ingredients is controlled without any adverse effect on other ingredients. As a result, the study focused on the agricultural active ingredient itself and found that the agricultural active ingredients are microencapsulated to a particular diameter with water-soluble materials such as gum arabic or α-cyclodextrin to improve their stability and further to improve physical and chemical properties of the preparations comprising said ingredients. According to further studies, we have achieved the present invention.

The present invention relates to an agricultural microcapsule of particular diameter of not more than 50 μm comprising agricultural active ingredients in water-soluble coating materials, an agricultural composition comprising the microcapsule, and production thereof.

The agricultural active ingredients may be either oily or solid. The solid ingredients include water-soluble type and water-insoluble type. Both types can be used for the present invention. Accordingly, the present invention can be applied to known insecticides, miticides, fungicides, herbicides, and any other active ingredients as pesticides.

Especially, the present invention advantageously enables solidifying of oily ingredients. Accordingly, the oily ingredients can be used like the conventional powder. In the present microcapsule, as the active ingredient is covered with water-soluble coating materials, interaction such as incompatibility may be controlled when the microcapsule is used as an admixture. It is hard for an active ingredient to appear on the surface of the microcapsule of the present invention.

The fungicides and insecticides which can be used for the present invention will be shown below. Symbols "S" and "L" show that ingredients marked "S" are soild at room temperature (1° to 30° C.) and "L" are liquid or oily.

Carbamate insecticides:
propoxur(S), isoprocarb(S), BPMC(S), xylylcarb(S), metolcarb(S), XMC(S), ethiofencarb(L), carbaryl(S), pirimicarb(S), bendiocarb(S), carbofuran(S), furathiocarb(L), carbosulfan(L), aminosulfulan, methomyl(S), cartap(S), fenoxycarb(S), alanycarb(S), cloethocarb(S), benfuracarb(L), fenothiocarb(S), etc.

Organophoshporus insecticides:
fenthion(L), fenitrothion(L), propaphos(L), cyanophos (L), prothiofos(L)., sulprofos(L), profenofos(L), EPN (L), cyanofenphos(S), acephate(S), oxydeprofos(L), disulfoton(L), thiometon(L), phenthoate(S), malathion (L), dimethoate(S), vamidothion(S), mecarbam(L), trichlorophon(S), naled(L), dichlorvos(L), chlorofenvinphos, tetrachlorvinphos(S), monocrotophos(S), phosalone(S), dialifos(S), chlorpyrifos-methyl(S), chlorpyrifos(S), pirimiphosmethyl(L), diazinon(L), etrimfos(L), pyridaphenthion(S), quinalphos(S), isoxathion(L), methidathion(S), salithion(S), pyraclophos(L), chlorthiophos(L), fortress(L), isofenphos(L), butathiofos, EDDP(L), etc.

Pyrethroids insecticides:
cyfluthrin(L), permethrin(L), cypermethrin(S), deltamethrin(S), cyhalothrin(L), fenpropathrin(S), fenvalerate(L), flucythrinate(L), flubalinate, ethofenprox(S), silanophane, fenpropathrin(S), tralomethrin(S), cycloprothrin(L), acrinathrin(S), etc.

Urea insecticides:
difulbenzuron(S), chlorfluazuron(S), nomolt(S), hexaflumuron(S), flufenxuron(S), diafenthiuron, flucycloxuron(S), hexythiazox(S), etc.

Other insecticides:
thiocyclam(S), buprofezin(S), bensultap(S), imidacloprid (S), hydroprene(S), fenazoquin, clofentezine(S), levamisol(S), dienochlor(S), cyromazine(S), fenpyroximate, pyridaben(S), pyriproxyfen(S), sufluramid, thiodicarb(S), nitenpyram(S), 1-(2-chloro-5-thiazolylmethyl)-3-methyl-2-nitroguanidine, etc.

Carbamate fungicides:

zineb(S), maneb(S), benomyl(S), thiophanate-methyl(S), cypendazole(S). carbendazim(S), prothiocarb(S), diethofencarb(S), etc.

Antibiotic fungicides:

validamycin A(S), kasugamycin(S), avermectin(S), milbemycin(S), etc.

Anilide fungicides:

mepronil(S), flutoluanil(S), pencycuron(S), carboxin(S), oxycarboxin(S), pyracarbolid(L), mebenil(S), furcarbanil, cyclafuramid(S), benodanil(S), granovax, metalaxyl(S), ofurace(S), benalaxyl(S), oxadixyl(S), cyprofuram(S), clozylacon, metsulfovax, tecloftalam (S), etc.

Organophosphorus fungicides:

edifenphos(L), IBP(L), pyrazophos, aliette, tolclofosmethyl(S), etc.

Azole fungicides:

fenarimol(S), flurprimidol(S), fluotrimazole(S), triadimefon(S), triadimenole(S), diclobutazol(S), paclobutazol, diniconazole(S), uniconazole(S), triflumizole(S), propiconazole(L), flutriafol(S), flusilazole(S); penconazole(S), prochloraz(S), triapenthenol(S), triarimol(S), fenarimol(S), bitertanol (S), imazalil(L), etaconazole(S), paclobutrazol(S), phenapronil, viniconazole, difenoconazole, bromuconazole, myclobutanil(S), hexaconazole(S), cyproconazole, furconazole-cis(S), fenethanil, tebuconazole(S), etc.

Dicarboxyimide fungicides:

dichlozoline(S), iprodione(S), vinclozolin(S), procymidone(S), myclozolin, fluoroimide(S), etc.

Other fungicides:

fthalide(S), monguard®(S), isoprothiolane(S), tricyclazole(S), probenazole(S), ferimzon(S), fluazinam(S), butiobate(L), pyroquilon(S), chlobenazone, TPN(S), captan(S), captafol(S), folpet (S), thiabendazole(S), fuberidazole(S), tridemorph(L), fenpropimorph(L), triforine(S), ethirimol(S), dimethirimol(S), hymexazol(S), ethazol(L), fenpropidin, pyrifenox(L), dilmethomorph(S), fenpiclonil, zarilamid, triclamide(S), flusulfamide, befran(S), dimfluazole, oxolinic acid(S), proxychlor, etc.

Pheromone:

okimeranolure(S), cherrytlure(L), diamolure(L), etc.

Other insecticides and fungicides:

fipronil, novaluron, flufenprox, fenpyrad or tebufenpyrad, methoxadiazone, benfluthrin, pyriproxyfen(S), diafenthiuron, dichlorfluanid, ftalaxyl, flapenazole, pipanipirim, thicyofen, opus®, ipconazole, dimetconazole, myxothiazol, thioimiconazole, quinconazole. etc.

Herbicides which can be used for the present invention will be shown below:

atrazine(S), cyanazine(S), ametryn(S), alachlor(S), butachloor(L), metolachlor(L), IPC(S), CIPC(S), thiobencarb(L), butylate(L), EPTC(L), dicamba(S), monuron(S), diuron(S), fluometuron(S), chloroxuron (S), benzthiazuron(S), karbutilate(S), metoxuron(S), methabenzthiazuron(S), chlorotoluron(S), isoproturon (S), trifluralin(S), pendimethalin(S), 2,4-D(S), MCPA (S), MCPP(S), molinate(L), epronaz(S), sethoxydim (L), alloxydim(S), tralkoxydim, fluazifop-butyl(L), quizalofop ethyl(S), fenoxaprop-ethyl(S), haloxyfop ethoxyethyl(S), fluazifop-P-butyl(L), framprof-M-isopropyl, tridiphane(S), methazole(S), oxadiazon(S), bentazone(S), pyrazolate(S), chlormethoxynil, chlornitrofen(S), dichlofop- methyl, oxyfluorfen(S), lactofen(L), achonifen(S), propanil(S), metribuzin(S), acifluorfen(S), fomesafen(S), bensulfuron methyl(S), chlorsulfuron(S), chlorimuron methyl(S), primisulfuron-methyl(S), triasulfuron(S), imazaquin (S), imazamethabenz(S), imazethapyr(S), tribenuron methyl(S), benzoylprop-ethyl(S), difenzoquat(S), Ioxynil(S), bifenox(S), clopyralid(S), mecoprop(S), metsulfuron-methyl(S), fluroxypyr(S), isoxaben(S), tiameturon-methyl, fluoroglycofen-ethyl(S), bromoxynil(S), pendimethalin(S), prometryn(S), pyrazosulfuron-ethyl(S), piperophos(L), esprocarb(L), pyributicarb(L), dithiopyr(S), HW-52(2',3'-dichloro-4-ethoxymethoxybenzanilide:S), benzofenap(S), benoxazol(L), bromobutide(S), chlomeprop, chlorthiamid(S), dalapon(L), dimepiperate(S), fluothiuron(S), chlornitrofen(S), MCPB(S), MCPCA, mefenacet(S), methoxyphenone(S), naproanilide(S), nitrofen(S), phenopylate(L), pyrazoxyfen(S), simetryn (S), swep(S), sinosulfuron, etc.

The water-soluble coating material used in the present invention means those readily soluble in water. Particularly, a water-soluble coating material having low crystallinity and a sp value of 5 to 40, preferably 10 to 30, is used. The sp value is generally well-known as a solubility parameter which shows an approximation between solute's polarity and solvent's. More preferbaly a water-soluble coating materials having a film-forming and/or clathrate activity are used.

Such materials include cyclodextrins and water-soluble polymers such as a water-soluble natural polymer, a water-soluble semi-synthetic polymer, a water-soluble synthetic polymer and the like.

Examples for the water-soluble natural polymer include starches, mannans, extracts from seaweeds, viscous substances from plants or microorganisms proteins, etc. The starches are exemplified as sweet potato starch, potato starch, tapioca starch, wheat starch, corn starch, etc. The mannans are exemplified as konjak mannan, etc. The extracts from seaweeds are exemplified as funori, agar, sodium alginate, etc. The viscous substances of plants are exemplified as *Abelmoschus manihot*, tragacanth gum, arabic gum, etc. The proteins are exemplified as glue, gelatin, casein, collagen, etc. Among those, water-soluble natural polymers such as viscous substances of plants are preferable, for example, arabic gum. The arabic gum is a water-soluble polysaccharide from *Acacia senegal, Acasia seyal* and the same kinds of plants, which has arabinose as a main element in its molecule.

Examples for the synthetic water-soluble polymer include polyvinyl alcohol, polyethylene oxide, polyacrylamide, sodium polyacrylate, polyvinyl pyrollidone, copolymer of methyl methacrylate, butyl methacrylate and dimethylaminoethyl methacrylate (Eudragit®), polycaprolactam, etc.

Examples for the semi-synthetic water-soluble polymer include water-soluble semi-synthetic celluloses, water-soluble semi-synthetic starches, etc. The water-soluble semi-synthetic celluloses are exemplified as viscose, methylcellulose, ethylcellulose, hydroxyethylcelllulose, carboxymethylcellulose, hydroxypropylcellulose, hydroxypropylmethylcellulose, etc. The water-soluble semi-synthetic starches are exemplified as water-soluble starch, carboxymethylated starch, dialdehyde-starch, dextrin, oxidized starch, etherified starch, esterified starch, etc. Among those, water-soluble semi-synthetic starches are preferable, for example, dextrin. Generally the detxrin includes four types of amylodextrin, erythrodextrin, achrodextrin and maltodextrin. All of those detxrins or mixtures thereof can be used in the present invention when they are water-soluble. As amylodextrin is in fact slightly soluble in cold water, the proportion of its content prefers to be lower. Preferrably erythrodextrin, achrodextrin, maltodextrin and a mixture containing mainly erythrodextrin and/or achrodextrin are used.

Molecular weight and degree of polymerization of the above-mentioned water-soluble polymers must not be limited, and should be determined according to kinds of monomers composing the polymer and to properties of the polymer itself. As mentioned before, any water-soluble coating materials can be used in the present invention when they are soluble in water and have film-forming activity. For example, in the case of dextrin, its molecular weight of not more than 10,000 is standerd and its range of 3,000 to 10,000 is preferable. Erythrodextrin and achrodextrin are preferred dextrins. In the case of polyvinyl alcohol, its average degree of polymertization of 300 to 3,000 is standard and its ragne of 300 to 2,000 is preferable. Particulary, in addition to that, its saponification ratio of 80 to 99 mol % is useful, preferrably 85 to 95 mol %. In the case of arabic gum, its molecular weight of 150,000 to 600,000 is standard, preferrably 240,000 to 580,000.

Examples for the cyclodextrins include α-, β-, τ-cyclodextrins, etc. Among those, α-cyclodextrin is preferable. Commercialized products are Toyoderin® (manufactured by TOYO JOZO Co., Ltd.: containing 50% of cyclodextrins, specially 30% of α-cyclodextrin), Isoelite®(manufactured by Nikken Chemical Co., Ltd.: containing 60% of α-cyclodextrin), etc.

The above-mentioned water-soluble coating materials can be mixed each other to be adopted to the present invention. Generally, supply of a natural polymer is precarious as its output is greatly affected by changes of climate. On the other hand, a synthetic polymer is preferable from a view point of its constant supply. Therefore, a mixture of water-soluble natural polymers and the other polymers is sometimes used. For example, mixtures of polyvinyl alcohol as a water-soluble synthetic polymer and arabic gum as a water-soluble natural polymer or dextrin as a water-soluble semi-synthetic polymer can be used in the present invention. In such cases, the proportion of synthetic polymers/the other polymers is not more than 2/1 (weight ratio), preferably in a range of 1/50 to 1/1.

Among the aforementioned materials, water-soluble natural polymer gum of viscous substance of plants, water-soluble semi-synthetic starches and cyclodextrin are preferable as a water soluble coating material. The concrete examples are arabic gum, α-cyclodextrin and dextrin. Specially, the most preferable water-soluble coating material is water-soluble natural polymer gum of viscous substance of plants such as arabic gum.

The ratio of the above agricultural active ingredient to the water-soluble material is 1/100 to 10/1 (by weight). Preferably, it is in the range from 1/20 to 5/1.

At such ratio, the diameter of the microcapsule comprising agricultural active ingredients in water-soluble coating materials is not larger than 50 μm. Preferably, the diameter is 3 to 45 μm, more preferably 5 to 40 μm.

The microcapsule having a diameter of not less than 50 μm has bad adhesion to plants as a dust formulation and fails to show the effect of the active ingredients. Further, when mixed with other active ingredients, a remarkable difference in density results in difficulty in sufficient mixing. On the other hand, the microcapsule comprising very fine particles of diameter of the order of 0 to 3 μm may drift away when sprayed, causing phytotoxicity and giving adverse effects to human bodies. As preparations aiming at prevention of such drift, DL (Drift-Less) dust has been known. For this purpose, as shown in the preferable embodiment of the present invention, dust formulation having a diameter of granule within the range from 3 to 45 μm, more preferably from 5 to 40 μm should be selected.

The production of the agricultural microcapsule of the present invention may be carried out according to the following processes:

1) Preparation of an aqueous solution, a suspension or an emulsion of the agricultural active ingredient and water-soluble coating material In general, the agricultural active ingredients are added to an aqueous solution of the water-soluble coating material. Using an emulsifier and stirrer, an aqueous solution, a suspension or an emulsion is prepared. The usable devices include a homomixer, a microfluidizer, a three-one motor, a die mill, etc. Such agitation may be carried out while heating if desired.

When the agricultural active ingredients are water-soluble, the raw powder may be directly dissolved to prepare an aqueous solution. When said active ingredients are water-insoluble, the raw materials may be ground to the powder having an average particle diameter of 0.1 to 10 μm, preferably 0.2 to 5 μm and a suspension is prepared. When the active ingredients are oily, they are prepared into an emulsion.

The amount of water used in this step may be optionally determined depending on the types of the water-soluble material or the active ingredients used. The amount is selected so that the concentrations of the water-soluble material and the active ingredients are not too high to become an obstacle of the following drying step. In general, the concentration of the water-soluble material is not more than 50%(W/V), preferably in the range of 2 to 50%(W/V). The viscosity of the resulting aqueous solution, suspension or emulsion is not more than 2,000 cp (25° C.), preferably not more than 1,000 cp.

The suspension or the emulsion may be produced to give the average particle diameter of the suspended particles or emulsified particles of 0.1 to 5 μm, preferable 0.2 to 3 μm. Particularly for production of an emulsion, desired emulsified particles are obtained by shearing and agitation.

2) Drying of the prepared solution

The solution prepared in the above step (1) is dried by suction drying or spray drying.

When drying is carried out by means of suction drying or the like, the dried product is ground and screened into particles smaller than a particular diameter.

Spray drying is effective to obtain microcapsule of its diameter within the given range. When drying is carried out by means of spray drying using a spray drier or the like, the drying conditions are optionally selected to give the product with the desired diameter. The temperature of spray-drying is in the range to be capable of removing water as a solvent from the solution prepared in the step (1). For example, drying step is carried out at the range of 50° to 250° C., preferably 70° to 200° C. The rotation speed of atomizer of a spray-dryer is instituted into the range to be capable of having the diameter of the obtained microcapsule be not more than 50μm, preferably in the range of 3 to 45μm, more preferably 5 to 40 μm.

More concrete example in which a spray-dryer L-8 type (manufactured by Okawara Kakoki Co.) is used is shown below. Emulsion, suspension or solution prepared in the step (1) is dried by hot air at 180° C. of inlet-temperature and at 110° C. of exit-temperature with rotation speed of the atomizer of 30,000rpm and the flow rate of the hot air of 30ml/min, to obtain microcapsules having a diameter of not more than 50μm. But the drying condition must not be limited to those mentioned above. Generally, the exit-temperature should be not less than 100° C. in order to avoid an adverse effect in that residual water in the obtained microcapsules may have a bad influence on stability of an active ingredient.

The microcapsule of the present invention can be obtained as shown above. Such microcapsule may contain necessary additives other than the agricultural active ingredients and the water-soluble coating materials. For example, a stabilizer characteristic of a certain kind of active ingredients may be added with the active ingredients to the solution prepared in the above step (1). Any agricultural active ingredients can be simultaneously subjected to the above steps (1) and (2) to give the microcapsuleof the present invention so long as said ingredients are not interactive.

Thus obtained microcapsule can be prepared to give an agricultural composition in the same manner as that of the conventional pesticidal powder.

The preparation using such agricultural composition includes, for example, dusts, DL dust, solified emulsifiable concentrate, water-dispersible powder, water-dispersible granules, seed treatment agent, particulate F. Particulary the microcapsule of the present invention can be effectively used for DL dust and solidified emulsifiable concentrate.

To prepare an admixture comprising two or more agricultural active ingredients, each of ingredients may be admixed together as a microcapsule of the present invention. Alternatively, a certain ingredient is solely adopted as microcapsule of the present invention. Particularly, when the oily active ingredient is admixed, said oily ingredient is microcapsulated according to the present invention to advantageously enable formulation by simple operation of powder mixing. When incompatible ingredients are admixed either ingredient is formed into the microcapsule of the present invention to enable formulation by simple operation of powder mixing controlling interaction due to said incompatibility.

Particulary, when the productions for admixtures of fenitrothion & ferimuzone, ferimuzone & cartap.hydrochloride, tricyclazole & fenitrithion, bensultap & BPMC, methomyl & cartap.hydrochloride and EDDP & pencycron, microcapsules of the present invention are useful. In these cases, it is preferable that an oily ingredient such as fenitrothion and an unstable ingredient should be microcapsulated according to the present invention, and then the microcapsules are admixed with the other ingredients.

The solid agricultural preparation itself may be produced by the known method. These preparations may comprise an agricultural auxiliary ingredients such as a dispersant, a spreader, a wetting agent, a thickener, a consolidation inhibitor, a coagulant, a binder, an antioxidant, a dewatering agent, etc., if desired.

As the conventional solid carrier and filler, one or more of the following materials and the like may be admixed:

1) mineral powder: clay (clay dust, kaolin, bentonite, Jaoanese acid clay, fuller's earth, etc.), talc (talc powder, agalmatolite powder, etc.), silica (diatomaceous earth powder, mica powder, etc.)
2) vegetable powder: soybean meal, tobacco powder, flour, wood meal, etc.
3) calcium carbonate, sulfur powder, urea powder, etc.

As the surfactant used as a dispersant, a spreader, a wetting agent or a penetrant, one or more nonionic or anionic surfactants may be admixed and used.

For example, nonionic surfactant
polyoxyethylene alkylaryl ether (Neugen EA-142®, HLB 14: manufactured by Dai-ichi Kogyo Seiyaku Co., Ltd.)
block copolymer of ethylene oxide and propylene oxide (Newpole PE-64®: manufactured by SANYO CHEMICAL INDUSTRIES, LTD), etc.

The HLB value of the nonion surfactant is preferably in the range of 8 to 18, more preferably 10 to 15.

anionic surfactant
polycarboxylic acid surfactant (Toxanone GR-30®; manufactured by SANYO CHEMICAL INDUSTRIES, LTD)
dialkylsulfosuccinate ester sodium salt (Neocol SW-C®; manufactured by Dai-ichi Kogyo Seiyaku Co., Ltd.)
sodium alkylnaphthalenesulfonate (Newcargen BX-C®; manufactured by Takemoto Yushi)
polyoxyethylene distyrenated phenyl ether sulfate ammonium salt (Dixzole 60A®; manufactured by Dai-ichi Kogyo Seiyaku Co., Ltd.)
sodium lignin sulfonate
potassium lignin sulfonate and the like.

Such surfactant is generally used in the range from 0 to 30 wt %, preferably from 0 to 20 wt % relative to the total amount of the preparation.

As fluidized auxiliaries, PAP auxiliary (isopropyl acid phosphate, etc.), talc and the like may be used. Such fluidizing auxiliaries are generally used within the range from 0 to 20 wt % preferably from 0 to 10 wt % relative to the total amount of the preparation.

As an anti-blocking agent, white carbon, diatomaceous earth, magnesium stearate, aluminum oxide, titanium dioxide, magnesium oxide, zinc oxide or the like may be used. Such anti-blocking agent is generally used within the range from 0 to 50 wt %, preferably from 0 to. 20 wt % relative to the total amount of the preparation.

As a coagulating agent, liquid paraffin, ethylene glycol, diethylene glycol, triethylene glycol, isobutylene polymer (IP solvent-2835®; Manufactured by Idemitsu Petroleum Chemical Co.) or the like may be used. Such coagulating agent is generally used within the range from 0 to 20 wt %, preferably from 0.2 to 10 wt % relative to the total amount of the preparation.

As a binder, sodium carboxymethylcellulose, dextrin, α-starch, polyvinyl alcohol, sodium lignin sulfonate, potassium lignin sulfonate, or the like may be used. Such binder is generally used within the range from 0 to 30 wt %, preferably from 0.2 to 10 wt % relative to the total amount of the preparation.

As an antioxidant, dibutylhydroxytoluene, 4,4-thiobis-6-tert-butyl-3-methylphenol, butylhydroxyanisole, p-octylphenol, mono-(di- or tri-)methylbenzylphenol, 2,6-tert-butyl-4-methylphenol, pentaerythritol-tetrakis[3-(3,5-di-tert-butyl-4-hydroxyphenyl)]propionate or the like may be used. Such antioxidant is generally used within the range from 0 to 30 wt %, preferably from 0 to 10 wt % relative to the total amount of the preparation.

As a desiccating agent, anhydrous gypsum, silicagel powder or the like may be used. Such desiccating agent is generally used within the range from 0 to 30 wt %, preferably from 0.5 to 20 wt % relative to the total amount of the preparation.

As ultraviolet absorbent, 2-(2'-hydroxy-5'-methylphenyl) benzotriazole, 2-ethoxy-2'-ethyloxazalic acid bisanilide, succinic acid dimethyl-1-(2-hydroxyethyl)-4-hydroxy-2,2,6,6-tetramethylpiperidine polycondensate or the like may be used. Such ultraviolet absorbent is generally used within the range from 0 to 20 wt %, preferably from 0.5 to 10 wt % relative to the total amount of the preparation.

As UV ray scattering agent, titanium dioxide or the like may be used. Such UV ray scattering agent is generally used within the range from 0 to 90 wt %, preferably from 1.0to 20 wt % relative to the total amount of the preparation.

Thus obtained solid preparation of various kinds may be sprayed and applied by the method according to the known method according to usage of the active ingredients contained therein.

Prescription of typical DL dust is shown below.

The agriculutural microcapsule 0.5 to 20 wt %

The other agricultural active ingredients 0 to 10 wt %

Solid carrier for DL dust 63.8 to 99.28 wt %

Coagulating agent 0.1 to 1.0 wt %

Antioxidant 0.02 to 0.2 wt %

Anti-blocking agent 0.1 to 5.0 wt %

The above-mentioned solid carrier for DL dust is clay for DL dust, kaolin, bentonite, diatomaceous earth powder, mica powder, agalmatolite powder and the like. The coagulating agent is liquid paraffin, ethylene glycol, isobutylene polymer (IP solvent-2835®; Manufactured by Idemitsu Petroleum Chemical Co.), polybutene and the like. The antioxidant is dibutylhydroxytoluene, 4,4-thiobis-6-tert-butyl-3-methylphenol, butylhydroxyanisole, pentaerythritol-tetrakis [3-(3,5-di-tert-butyl-4-hydroxyphenyl)]propionate and the like. The anti-blocking agent is white Carbon, diatomaceous earth, magnesium stearate, aluminum oxide, titanium dioxide, magnesium oxide, zinc oxide and the like. The active ingredients for a paddy field are effective. The active ingredient is used alone or as a mixture. For example, fenitrothion, tricyclazole, ferimzone, validamycine A, cartap.hydrochloride, fthalide, ethofenprox, bensultap, buprofezin, isoprothiolane. BPMC are used. Specially agricultural admixtures of ferimuzone & fenitrothion, fenitrothion & tricyclazole and ferimuzone & cartap.hydrochloride are effective. In such cases, ferimuzone and fenitrothion should be microcapsulated according to the present invention. The particle size of the obtained DL dust is in the range of 5 to 50 μm, preferably 10 to 50 μm.

By using the obtained DL dust, decomposition of an active ingredient can be controlled easily. The DL dust can be stored for a long term. An oily active ingredient can be solidified as powder according to the presnt invention and the powder preparation has an improved physical and chemical properties. As a results, the obtained DL dust can be easily scattered to an agricultural field evenly. Moreover, as a water-soluble coating material is used as a coating substance for microcapsules, the DL dust's adhesiveness to plants is extremely improved, and its biological activity can be enhanced.

Prescription of typical solidified emulsifiable concentrate is shown below.

Oily active ingredient 5.0 to 60 wt %

Water-soluble coating material 10.0 to 94.6 wt %

Surfactant (HLB: 2 to 8) 0.2 to 20 wt %

Surfactant (HLB: 10 to 19) 0.2 to 10 wt %

As the above mentioned surfactants nonionic surfantants are used. Particulary, both of one of HLB 2 to 8 and the other of HLB 10 to 19 are preferably used jointly. The one of HLB 2 to 8 is sorbitan alkylate, polyoxyethylene nonylphenylether or the like. The one of HLB 10 to 19 is polyoxyethylene alkylarylether, polyoxyethylene sorbitan monooleate, polyoxyethyelene lanoline alcohole ether or the like. The active ingredients for a paddy field are useful. The active ingredient is used alone as a mixture. Oily active ingredients such as pyraclofos, fenitrothion, ethofenprox, malathion, PAP, propaphos, IBP and the like are used. Microcapsules of the present invention can be applied as solidified emulsifiable concentrate itself. The concentrate can be prepared by emulsifying the above-mentioned composition with water and spray-drying it according to the present invention. In this case, arabic gum is preferred as water-soluble coating materials. Diameter of the Solidified emulsifiable concentrate is in the range of 10 to 50 μm. preferably 20 to 50 μm.

As the concentrate can be prepared without organic solvent, its safety for human and environment is exceed. The concentrate can be wrapped without using a glass bottle, merely by using a paper bag or the like. Thereofre, a serious environmental problem such as waste of packages for conventional emulsifiable concentrates is solved by the present invention. When water-soluble film is used as a package for the concentrate, emulsion for scattering is easily prepared without directly contacting chemicals as pesticide. Such a way is also very safe for an operator.

The solid agricultural preparation obtained as mentioned before can be applied or scattering to an agricultural field according to a conventional method determined by the active ingredients comprised in it.

The agricultural microcapsule of the present invention has the following advantages:

(1) Even liquid agricultural active ingredients can be readily solidified as powder.

(2) It is easy to handle the microcapsules.

(3) The microcapsulea are useful raw materials for solid agricultural composition.

(4) It is easy to have an active ingredient be stable.

(5) An admixture wherein incompatible agricultural active ingredients are mixed may be readily obtained.

(6) Such admixture is excellent in storage stability.

(7) Even in the admixture, it is easy to have an active ingredient be stable.

(8) By a spray-drying method, the microcapsules having almost uniform particle size can be obtained.

(9) The microcapsules obtained by spray-drying have excellent fluidity and dispersability.

(10) DL dust can be easily prepared by using the microcapsules obtained by spray-drying.

(11) The DL dust's adhesiveness to plants is excellent.

(12) Organic solvent is not necessary to prepare solidified emulsifiable concentrate of the microcapsule. The preparation has reduced toxicity to humans and environment and alleviates package-waste problmes.

[EXAMPLES]

The present invention will be illustrated in more detail in the following examples, reference examples, experimental examples.

Example 1

Mixed DL Dust (Fenitrothion and Ferimzone)

(1) Preparation for microcapsules of fenitrothion

Gum arabic (300 g) was dissolved in water (7,500 g), to which was added fenitrothion (Sumithion®: purity, 96.8 %, manufactured by SUMITOMO CHEMICAL COMPANY LIMITED) (81 g). The mixture was emulsified using a microfluidizer (13,000 psi, 1 pass) to give an emulsion. The viscosity of the emulsion was 110 cp(25° C.) and an average diameter of emulsified particule was 0.8 μm.

Water was evaporated to driness from this emulsion using a spray drier (inlet temperature: 220° C., rotation speed of atomizer: 30,000 rpm) to give fenitrothion microcapsules having a diameter of 5 to 30 μm (fenitrothion content; 20%).

(2) Preparation for mixed DL dust of fenitrothion and ferimzone

The thus obtained fenitrothion microcapsules (15 parts by weight), ferimzone (2 parts by weight), white carbon (2 parts by weight), liquid paraffin (1 part by weight), clay (80 parts by weight) were weighed and mixed by a chaser mill, and further remixed by a flush mixer to obtain DL dust. The diameter of the DL dust was in the range of 10 to 45 μm.

Example 2

Mixed DL Dust (Fenitrothion and Ferimzone)

(1) Preparation for microcapsules of fenitrothion

One hundred grams of cyclodextrine containing mainly α-cyclodextrin (manufactured by TOYO JOZO Co. Ltd.: Toyodeline P® containing 50% of cyclodextrins, specially 30% of α-cyclodextrin) was dissolved in water (500 g), to which was added fenitrothion (purity, 96.8%, manufactured by SUMITOMO CHEMICAL COMPANY LIMITED) (46 g). The mixture was emulsified using a microfluidizer (13,000 psi, 1 pass) to give an emulsion. The viscosity of the emulsion was 120 cp(25° C.) and an average diameter of emulsified particule was 1.9 μm.

Water was evaporated to driness from this emulsion using a spray drier (inlet temperature: 220° C., rotation speed of atomizer: 30,000 rpm) to give fenitrothion microcapsules having a diameter of 5 to 30 μm (fenitrothion content: 30%).

An emulsion of fenitrothion for scattering was obtained by diluting 2 g of the obtained fenitrothion microcapsules to 1,000 ml of water without compulsory stirring.

(2) Preparation for mixed DL dust of fenitrothion and ferimzone

The thus obtained fenitrothion microcapsules (10 parts by weight), ferimzone (2 parts by weight), white carbon (2 parts by weight), liquid paraffin (1 part by weight), clay (85 parts by weight) were weighed and DL dust was obtained in the same manner as described in Example 1. The diameter of the DL dust was in the range of 10 to 45 μm.

Example 3

Mixed DL Dust (Fenitrothion and Tricyclazole)

Fenitrothion microcapsules obtained in Example 1 (10 parts by weight), tricyclazole (1 parts by weight), liquid paraffin (1 part by weight), clay (83 parts by weight) were weighed and DL dust was obtained in the same manner as described in Example 1. The diameter of the DL dust was in the range of 10 to 45 μm.

Example 4

Mixed DL Dust (Fenitrothion and Tricyclazole)

Fenitrothion microcapsules obtained in Example 2 (6.7 parts by weight), tricyclazole (1 parts by weight), liquid paraffin (1 part by weight), clay (88 parts by weight) were weighed and DL dust was obtained in the same manner as described in Example 1. The diameter of the DL dust was in the range of 10 to 45 μpm.

Example 5

DL Dust (Nitenpyram)

(1) Preparation for microcapsules of nitenpyram

Ninety grams of cyclodextrine containing mainly α-cyclodextrin (manufactured by TOYO JOZO Co. Ltd.; Toyodeline P® containing 50% of cyclodextrins, specially 30% of α-cyclodextrin) was dissolved in water (225 g), to which was added 10 g of nitenpyram (purity, 100%, manufactured by Takeda Chemical Industries, Ltd.). Water of the solution was evaporated to driness from this solution using a spray drier (inlet temperature: 220° C., rotation speed of atomizer; 30,000 rpm) to give nitenpyram microcapsules having a diameter of 5 to 40 μm (nitenpyram content; 10%).

(2) Preparation for DL dust of nitenpyram

The thus obtained nitenpyram microcapsules (2.5 parts by weight), liquid paraffin (10 part by weight), white carbon (0.5 part by weight), gypsum anhydride (15.8 parts by weight) and clay (81 parts by weight) were weighed and mixed by a chaser mill, and further grounded by a vandum mill to obtain a DL dust. The diameter of the DL dust was in the range of 10 to 45 μm.

Example 6

Mixed DL Dust (Bensultap and BPMC)

(1) Preparation for microcapsules of BPMC

Two hundred and seventy grams of cyclodextrine containing mainly α-cyclodextrin (manufactured by TOYO JOZO Co. Ltd.; Toyodeline P® containing 50% of cyclodextrins, specially 30% of α-cyclodextrin) was dissolved in water (1,000 g), to which was added 30 g of BPMC (purity, 99%). The mixture was emulsified using a microfluidizer (13,000 psi, 1 pass) to give an emulsion. The viscosity of the emulsion was 95 cp(25° C.) and an average diameter of emulsified particule was 1.1 μm.

Water was evaporated to driness from this emulsion using a spray drier (inlet temperature; 220° C., rotation speed of atomizer; 30,000 rpm) to give BPMC microcapsules having a diameter of 10 to 50 μm (BPMC content: 10%).

(2) Preparation for mixed DL dust of bensultap and BPMC

The thus obtained BPMC microcapsules (30 parts by weight), bensultap (2 parts by weight), zinc oxide (5 parts by weight), white carbon (5 parts by weight), isopropyl phosphate (0.6 part by weight), liquid paraffin (0.5 part by weight), clay (56.9 parts by weight) were weighed and mixed by a chaser mill, and further grounded by a vandum mill to obtain a DL dust. The diameter of the DL dust was in the range of 10 to 45 μm.

Example 7

Mixed DL Dust (Fenitrothion, Fthalide, Cartap and Ethofenprox)

(1) Preparation for microcapsules of ferimzone

Gum arabic (300 g) was dissolved in water (466 g), to which was added 100 g of ferimzone (purity 98.7%, manufactured by Takeda Chemical Industries Ltd.). The mixture was suspended and grounded by using die mill (flow rate: 15 m/sec, 1 pass) to give a suspension. The viscosity of the suspension was 128 cp(25° C.) and an average diameter of suspended particule was 2.2 μm.

Water was evaporated to driness from this suspension using a spray drier (inlet temperature: 220° C., rotation speed of atomizer; 30,000 rpm) to give ferimzone microcapsules having a diameter of 5 to 50 μm (ferimzone content; 50%).

(2) Preparation for mixed DL dust of fenitrothion, fthalide, cartap and ethofenprox The thus obtained ferimzone microcapsules (4 parts by weight), fthalide (1.5 parts by weight), cartap.hydrochloride (2 parts by weight), ethofenprox (0.5 part by weight), liquid paraffin (1.0 part by weight), antioxidant of phenol compound (Irganox-1010®, 0.05 part by weight), 1-phenyl-1-xylylethane (SAS-296®, manufactured by Misseki Co., 0.4 part by weight), white carbon (1.25 parts by weight), isopropyl phosphate (0.25 part by weight), clay (89 parts by weight) were weighed and mixed by a chaser mill, and grounded by vandum mill to obtain DL dust. The diameter of the DL dust was in the range of 10 to 45 µm.

Example 8

Microcapsules of Ethofenprox

Two hundred and seventy grams of cyclodextrine containing mainly α-cyclodextrin (manufactured by TOYO JOZO Co. Ltd.; Toyodeline P® containing 50% of cyclodextrins, specially 30% of α-cyclodextrin) was dissolved in water (1,000 g), to which was added 30 g of ethofenprox (purity, 97%). The mixture was emulsified using a microfluidizer (13,000 psi, 1 pass) to give an emulsion. The viscosity of the emulsion was 68 cp(25° C.) and an average diameter of emulsified particule was 0.7 µm. The procedures were then carried out as in Example 2 to give ethofenprox microcapsules having a diameter of 5 to 50 µm (ethofenprox content; 10%).

Example 9

Microcapsules of Fenitrothion

Fifty grams of arabic gum and 50 g of polyvinyl alcohole (saponifized degree: 88 mol %, average degree of polimerization: 400) were dissolved in 1,150 g of water, to which was added 150 g of fenitrothion (Sumithion®, purity, 96.8%, manufactured by SUMITOMO CHEMICAL CO.). The mixture was emulsified using a microfluidizer (13,000 psi, 1 pass) to give an emulsion. The viscosity of the emulsion was 185 cp(25° C.) and an average diameter of emulsified particule was 0.9 µm. The procedures were then carried out as in Example 1 to give fenitrothion microcapsules having a diameter of 10 to 50 µm (fenitrothion content; 60%).

Example 10

Microcapsules of Fenitrothion

One hundred and forty grams of dextrin (Pinedex#3®, manufactured by Matsutani Chemical Industries Ltd.) was dissolved in 327 g of water, to which was added 60 g of fenitrothion (Sumithion®, purity, 96.8%, manufactured by SUMITOMO CHEMICAL CO.). The mixture was emulsified using a microfluidizer (13.000 psi, 1 pass) to give an emulsion. The viscosity of the emulsion was 136 cp(25° C.) and an average diameter of emulsified particule was 1.8 µm. The following procedures were carried out by the same as Example 1 to give fenitrothion microcapsules having a diameter of 5 to 50 µm (fenitrothion content: 30%).

Example 11

Microcapsules of Fenitrothion

One hundred and eighty grams of dextrin (Oilque®, manufactured by Nichiden Chemical Co.) and 20 g of polyvinylalcohole (saponifized degree: 88 mol %, average degree of polimerization: 400) were dissolved in 900 g of water, to which was added 86 g of fenitrothion (Sumithion®, purity, 96.8%, manufactured by SUMITOMO CHEMICAL CO.). The mixture was emulsified using a microfluidizer (13,000 psi, 1 pass) to give an emulsion. The viscosity of the emulsion was 86 cp(25° C.) and an average diameter of emulsified particule was 0.75 µm. The procedures were then carried out as in Example 1 to give fenitrothion microcapsules having a diameter of 5 to 40 µm (fenitrothion content: 30%).

Example 12

Microcapsules of Pyraclofos (Solidified Emulsifiable Concentrate)

Fifty grams of arabic gum was dissolved in 200 g of water, to which was added 35 g of pyraclofos (purity 93%, manufactured by Takeda Chemical Industries, Ltd.), 13.5 g of sorbitan alkylate (NKD935®: HLB 4.3) and 1.5 g of nonionic surfactant of characteristic polymer (NKD3020®: HLB 19.0). The mixture was emulsified using a microfluidizer (13,000 psi, 1 pass) to give an emulsion. The viscosity of the emulsion was 70 cp(25° C.) and an average diameter of emulsified particule was 1.3 µm. The following procedures were carried out by the same as Example 1 to give pyraclofos microcapsules having a diameter of 5 to 50 µm (pyraclofos content: 35%). The obtained microcapsules were applied as a solidified emulsifiable concentrate.

Example 13

Mixed DL Dust (Fenitrothion, Ferimzone, Fthalide and Ethofenprox)

(1) Preparation for microcapsules of fenitrothion

Gum arabic (140 g) was dissolved in water (560 g), to which was added fenitrothion (Sumithion®; purity, 96.8%, manufactured by SUMITOMO CHEMICAL COMPANY LIMITED) (60 g). The mixture was emulsified using a microfluidizer (13,000 psi, 1 pass) to give an emulsion. The viscosity of the emulsion was 124 cp(25° C.) and an average diameter of emulsified particule was 1.3 µm.

Water was evaporated to driness from this emulsion using a spray drier (inlet temperature: 220° C., rotation speed of atomizer: 30,000 rpm) to give fenitrothion microcapsules having a diameter of 5 to 50 µm (fenitrothion content: 30%).

(2) Preparation for mixed DL dust of fenitrothion, ferimzone, fthalide and ethofenprox The thus obtained ferimzone microcapsules (10 parts by weight), ferimzone (2 parts by weight), fthalide (1.5 parts by weight), ethofenprox (0.5 part by weight), white carbon (2 parts by weight), pentaerythritol-tetrakis[3-(3,5-di-tert-butyl-4-hydroxyphenyl)]propionate (0.05 part by weight), 1-phenyl-1-xylylethane (SAS-296®, manufactured by Nisseki Go., 0.45 part by weight), clay (82.5 parts by weight) were weighed and mixed by a nauta mixer, and further remixed by frush mixer to obtain DL dust. The diameter of the DL dust was in the range of 5 to 50 µm.

Reference Example 1

Mixed DL Dust(Ferimzone and Fenitrothion)

Ferimzone (2 parts by weight), fenitrothion (3 parts by weight), white carbon (2 parts by weight), liquid paraffin (1 part by weight) and clay (92 parts by weight) were weighed and mixed in a chaser mill. The resultant was further remixed by a flush mixer to give a DL dust having a diameter of 5 to 50 µm.

Reference Example 2

Mixed DL Dust(Fenitrothion and Tricyclazole)

Tricyclazole (1 part by weight), fenitrothion (2 parts by weight), liquid paraffin (1 part by weight) and clay (96 parts by weight) were weighed and DL dust having a diameter of 5 to 50 μm was obtained in the same manner as described in Reference Example 1.

Reference Example 3

Mixed DL Dust(Ferimzone and Fenitrothion)

Fenitrothion (3 parts by weight), gum arabic (20 parts by weight) were weighed and mixed by a chaser mill, Ferimzone (2 parts by weight), white carbon (3 parts by weight), liquid paraffin (1 part by weight) and clay (71 parts by weight) were weighed and added to the powder mixture, then mixed by a chaser mill. The resultant was further remixed by a flush mixer to give a DL dust having a diameter of 5 to 50 μm.

Reference Example 4

DL Dust (Nitnpyram)

Nitenpyram (0.25 part by weight), liquid paraffin (1.0 part by weight), white carbon (0.5 part by weight) and clay (98.25 parts by weight) were weighed and mixed in a chaser mill. The resultant was further remixed by a flush mixer to give a DL dust having a diameter of 5 to 50 μm.

Reference Example 5

Mixed DL Dust (BPMC-Bensultap)

BPMC (3 parts by weight), bensultap (2 parts by weight), zinc oxide (5 parts by weight), isopropyl phosphate (0.6 part by weight), liquid paraffin (0.5 part by weight) and clay (83.9 parts by weight) were weighed and mixed in a chaser mill. The resultant was further remixed by a flush mixer to give a DL dust having a diameter of 5 to 50 μm.

Reference Example 6

Mixed DL Dust (Fenitrothion, Fthalide, Cartap and Ethofenprox)

Ferimzone (2 parts by weight), fthalide (1.5 parts by weight), cartap.hydrochloride (2 parts by weight), ethofenprox (0.5 part by weight), liquid paraffin (1.0 part by weight), antioxidant of phenol compound (Irganox1010®, 0.05 part by weight), 1-phenyl-1-xylylethane (SAS-296®, manufactured by Nisseki Co., 0.45 part by weight), white carbon (1.25 parts by weight), isopropyl phosphate (0.25 part by weight), clay (91 parts by weight) were weighed and mixed by a chaser mill, and grounded by vandum mill to obtain DL dust having a diameter of 5 to 50 μm.

Reference Example 7

DL dust (Fenitrothion)

Fenitrothion (3 parts by weight), isopropyl phosphate (0.5 part by weight), liquid paraffin (1.0 part by weight), white carbon (3 parts by weight) and clay (92.5 parts by weight) were weighed and mixed in a chaser mill. The resultant was further remixed by a flush mixer to give a DL dust having a diameter of 5 to 50 μm.

Experimental Example 1

Stability of Active Ingredients

Each of 20 g of the samples (DL dusts) obtained in Examples 1 to 7 and Reference Examples 1 to 6 were respectively placed and sealed in sample bottles, then stored at 40° C. for a month. Subsequently, the samples were immediately removed and content of the active ingredient was measured using HPLC. The results of the experiment are shown in Table 1. Decomposition rate (%) was obtained using the following formula:

$$\text{Decomposition Rate (\%)} = \frac{\text{(Initial content of the active ingredient)} - \text{(Residual content of the active ingredient)}}{\text{(Initial Content of the active ingredient)}} \times 100$$

TABLE 1

| Sample | Decomposition Ratio after storage at 40° C. for one month (%) | | | | | |
| --- | --- | --- | --- | --- | --- | --- |
| | A | B | C | D | E | F |
| Ex. 1 | 5.2 | 4.8 | | | | |
| Ref. Ex. 1 | 94.5 | 56.1 | | | | |
| Ex. 2 | 14.7 | 3.2 | | | | |
| Ref. Ex. 3 | 91.8 | 60.5 | | | | |
| Ex. 3 | 2.3 | | 0.7 | | | |
| Ex. 4 | 8.5 | | 4.6 | | | |
| Ref. Ex. 2 | 90.4 | | 88.6 | | | |
| Ex. 5 | | | | 1.6 | | |
| Ref. Ex. 4 | | | | 10.8 | | |
| Ex. 6 | | | | | 9.1 | |
| Ref. Ex. 5 | | | | | 30.1 | |
| Ex. 7 | | 1.5 | | | | 1.8 |
| Ref. Ex. 6 | | 6.0 | | | | 16.8 |

Note)
A: Fenitrothion,
B: Ferimzone,
C: tricyclazole,
D: Nitenpyram,
E: Bensultap,
F Cartap

Experimental Example 2

Effects of Agricultural Preparations

Insecticidal effects to Brown rice planthopper (*Nilaparvata lugens*, third-larvae) and Green rice leafhopper (*Nephotettix cincticep.* third-larvae) for DL dusts obtained in Examples 3 & 4 and Reference Example 7 were investigated by using 2-leaf-stage rice seedlings.

Predetermined amounts (10, 30 and 90 mg/stump as an amount of the active ingredient) of each of the samples were scattered to leaves of rice seedling at 2-leaf stage, and then, the seedling were transferred to test tubes. Ten Brown rice planthoppers were released in the tube at the same day of sample-scattering (28±1° C.). Ten Green rice leafhoppers were released in the tube one day after the scatterng (28±1° C.). The number of survived insects was calculated one day or two days after the releases. The results of the experiment was shown in Table 2. Mortality (%) was obtained using the following formula:

$$\text{Mortality (\%)} = \frac{\text{(Number of the released insects)} - \text{(Number of the survived insects)}}{\text{(Number of the released insects)}} \times 100$$

TABLE 2

| Sample | Dose | Brown rice planthopper | | Green rice leafhopper | |
|---|---|---|---|---|---|
| | | 1 day after | 2 days after | 1 day after | 2 days after |
| Ex. 3 | 10 | 0 | 3 | 13 | 20 |
| | 30 | 0 | 10 | 37 | 47 |
| | 90 | 70 | 87 | 77 | 80 |
| Ex. 4 | 10 | 0 | 0 | 17 | 27 |
| | 30 | 20 | 27 | 40 | 53 |
| | 90 | 70 | 80 | 70 | 83 |
| Ref. Ex. 7 | 10 | 0 | 0 | 10 | 23 |
| | 30 | 0 | 0 | 20 | 43 |
| | 90 | 47 | 63 | 60 | 70 |
| Control | — | 0 | 0 | 0 | 0 |

Note)
Figures in the table show average mortality (%).
Control: No agent is scattered to rice seedlings.

What we claimed is:

1. A process for production of an agricultural microcapsule having a diameter of not more than 50 µm, which comprises an agricultural active ingredient in gum arabic, the process comprising:
   (i) dispersing or emulsifying the agricultural active ingredient in a solution dissolving gum arabic to give a mixture wherein the average diameter of a suspended particle in the mixture is from 0.1 µm to 5 µm; and
   (ii) spray-drying the mixture.

2. A process for production of an agricultural microcapsule as claimed in claim 1, wherein a drying temperature of the spray-dry is in the range of 50° to 250° C.

3. A process for production of an agricultural microcapsule as claimed in claim 1, wherein the concentration of gum arabic in the solution is not more than 50% (W/V).

4. A process for production of an agricultural microcapsule as claimed in claim 1, wherein the viscosity of the mixture is not more than 2,000 cp at 25° C.

5. A process for the production of an agricultural microcapsule as claimed in claim 1, wherein the average diameter of an emulsified particle in the mixture is in the range of 0.1 to 5.0 µm.

6. A process for production of an agricultural microcapsule as claimed in claim 1, wherein a weight ratio of the active ingredient/gum arabic is in the range of 1/100 to 10/1.

7. A process for production of an agricultural microcapsule as claimed in claim 1, wherein the agricultural active ingredient is an oil at ordinary temperature.

8. An agricultural microcapsule having a diameter of not more than 50 µm, which is obtained by the process of claim 1, wherein the agriculturally active ingredient is an oil at ordinary temperature.

9. An agricultural microcapsule having a diameter of not more than 50 µm, which comprises an agricultural active ingredient in gum arabic, wherein the agriculturally active ingredient is an oil at ordinary temperature.

10. An agricultural microcapsule as claimed in claim 9, wherein the weight ratio of the active ingredient/gum arabic is in the range of 1/100 to 10/1.

11. An agricultural composition comprising:
    an agricultural microcapsule having a diameter of not more than 50 µm, which comprises an agriculturally active ingredient in gum arabic; and
    an agriculturally useful carrier, wherein the agriculturally active ingredient is an oil at ordinary temperature.

12. An agricultural composition as claimed in claim 11, wherein the weight ratio of the active ingredient/gum arabic is in the range of 1/100 to 10/1.

13. An agricultural composition as claimed in claim 11 which is a solidified emulsifiable concentrate.

14. An agricultural composition as claimed in claim 11 which is a solidified emulsifiable concentrate comprising:
    (i) 5.0 to 60 wt % of an agricultural oily active ingredient;
    (ii) 10.0 to 94.6 wt % of gum arabic;
    (iii) 0.2 to 20 wt % of surfactant having HLB of 2 to 8; and
    (iv) 0.2 to 10 wt % of surfactant having HLB of 10 to 19, wherein the active ingredient and both of the surfactants are in the gum arabic.

15. An agricultural composition as claimed in claim 11 which is DL dust.

16. An agricultural composition as claimed in claim 11 which is DL dust comprising:
    (i) 0.5 to 20 wt % of an agricultural microcapsule having a diameter of not more than 50 µm, which comprises an agriculturally active ingredient in gum arabic, wherein the agriculturally active ingredient is an oil at ordinary temperature;
    (ii) 0 to 10 wt % of an active ingredient which is incompatible to the active ingredient in the microcapsule;
    (iii) 63.8 to 99.28 wt % of solid carrier;
    (iv) 0.1 to 1.0 wt % of coagulant;
    (v) 0.02 to 0.2 wt % of antioxidant; and
    (vi) 0.1 to 5.0 wt % of anti-blocking agent, wherein diameter of the DL dust is in the range of 5 to 50 µm.

* * * * *